United States Patent
Locke et al.

(10) Patent No.: US 10,632,020 B2
(45) Date of Patent: Apr. 28, 2020

(54) HYBRID DRAPE HAVING A GEL-COATED PERFORATED MESH

(71) Applicant: KCI Licensing, Inc., San Antonio, TX (US)

(72) Inventors: Christopher Brian Locke, Bournemouth (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 482 days.

(21) Appl. No.: 14/619,714

(22) Filed: Feb. 11, 2015

(65) Prior Publication Data
US 2015/0245949 A1 Sep. 3, 2015

Related U.S. Application Data

(60) Provisional application No. 61/945,882, filed on Feb. 28, 2014.

(51) Int. Cl.
*A61M 1/00* (2006.01)
*A61F 13/00* (2006.01)
(Continued)

(52) U.S. Cl.
CPC ...... *A61F 13/025* (2013.01); *A61F 13/00068* (2013.01); *A61F 13/0216* (2013.01);
(Continued)

(58) Field of Classification Search
CPC .............. A61F 13/025; A61F 13/00068; A61F 13/0216; A61F 13/0253; A61F 13/0283; C09J 7/00; B32B 2405/00
See application file for complete search history.

(56) References Cited

U.S. PATENT DOCUMENTS 1,355,846 A 10/1920 Rannells
1,944,834 A 1/1934 Bennett
(Continued)

FOREIGN PATENT DOCUMENTS

AU 550575 A1 3/1986
AU 550575 B2 3/1986
(Continued)

OTHER PUBLICATIONS

European Search Report for corresponding Application No. 15194949.2.
(Continued)

*Primary Examiner* — Adam Marcetich
*Assistant Examiner* — Jessica R Arble (57) ABSTRACT

A system for treating a tissue site with negative-pressure is described. The system includes a manifold configured to be positioned adjacent to the tissue site and a drape configured to be positioned over the tissue site and the manifold to form a sealed space. The system also includes a negative-pressure source configured to provide negative-pressure to the sealed space. The drape includes a film layer, a layer of a bonding adhesive coupled to the film layer, and a mesh coupled to the layer of the bonding adhesive. The mesh includes a coating of a sealing adhesive and one or more bonding apertures. Methods of manufacturing the drape are also described.

34 Claims, 4 Drawing Sheets

(51) Int. Cl.
*A61F 13/02* (2006.01)
*A61L 15/58* (2006.01)
(52) U.S. Cl.
CPC ...... *A61F 13/0253* (2013.01); *A61F 13/0283* (2013.01); *A61L 15/58* (2013.01); *A61M 1/0088* (2013.01); *Y10T 156/1062* (2015.01)

(56) References Cited

U.S. PATENT DOCUMENTS

| | | | |
|---|---|---|---|
| 2,547,758 A | 4/1951 | Keeling | |
| 2,552,664 A | 5/1951 | Burdine | |
| 2,632,443 A | 3/1953 | Lesher | |
| 2,682,873 A | 7/1954 | Evans et al. | |
| 2,860,081 A | 11/1958 | Eiken | |
| 2,910,763 A | 11/1959 | Lauterbach | |
| 2,969,057 A | 1/1961 | Simmons | |
| 3,066,672 A | 12/1962 | Crosby, Jr. et al. | |
| 3,172,808 A | 3/1965 | Baumann et al. | |
| 3,183,116 A | 5/1965 | Schaar | |
| 3,367,332 A | 2/1968 | Groves | |
| 3,376,868 A | 4/1968 | Mondiadis | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,742,952 A | 7/1973 | Magers et al. | |
| 3,774,611 A | 11/1973 | Tussey et al. | |
| 3,777,016 A | 12/1973 | Gilbert | |
| 3,779,243 A | 12/1973 | Tussey et al. | |
| 3,826,254 A | 7/1974 | Mellor | |
| 3,852,823 A | 12/1974 | Jones | |
| 3,903,882 A | 9/1975 | Augurt | |
| 3,967,624 A | 7/1976 | Milnamow | |
| 3,983,297 A | 9/1976 | Ono et al. | |
| 4,060,081 A | 11/1977 | Yannas et al. | |
| 4,080,970 A | 3/1978 | Miller | |
| 4,096,853 A | 6/1978 | Weigand | |
| 4,139,004 A | 2/1979 | Gonzalez, Jr. | |
| 4,141,361 A | 2/1979 | Snyder | |
| 4,163,822 A | 8/1979 | Walter | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,360,015 A * | 11/1982 | Mayer ............... | A61F 13/00029 602/47 |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,414,970 A | 11/1983 | Berry | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,529,402 A | 7/1985 | Weilbacher et al. | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,600,146 A | 7/1986 | Ohm | |
| 4,605,399 A | 8/1986 | Weston et al. | |
| 4,608,041 A | 8/1986 | Nielsen | |
| 4,617,021 A | 10/1986 | Leuprecht | |
| 4,640,688 A | 2/1987 | Hauser | |
| 4,655,754 A | 4/1987 | Richmond et al. | |
| 4,664,652 A | 5/1987 | Weilbacher | |
| 4,664,662 A | 5/1987 | Webster | |
| 4,710,165 A | 12/1987 | McNeil et al. | |
| 4,715,857 A | 12/1987 | Juhasz et al. | |
| 4,733,659 A | 3/1988 | Edenbaum et al. | |
| 4,743,232 A | 5/1988 | Kruger | |
| 4,753,230 A | 6/1988 | Carus et al. | |
| 4,753,232 A * | 6/1988 | Ward ................... | A61F 13/023 602/52 |
| 4,758,220 A | 7/1988 | Sundblom et al. | |
| 4,787,888 A | 11/1988 | Fox | |
| 4,826,494 A | 5/1989 | Richmond et al. | |
| 4,832,008 A | 5/1989 | Gilman | |
| 4,838,883 A | 6/1989 | Matsuura | |
| 4,840,187 A | 6/1989 | Brazier | |
| 4,848,364 A | 7/1989 | Bosman | |
| 4,863,449 A | 9/1989 | Therriault et al. | |
| 4,871,611 A | 10/1989 | LeBel | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,930,997 A | 6/1990 | Bennett | |
| 4,941,882 A | 7/1990 | Ward et al. | |
| 4,953,565 A | 9/1990 | Tachibana et al. | |
| 4,961,493 A | 10/1990 | Kaihatsu | |
| 4,969,880 A | 11/1990 | Zamierowski | |
| 4,981,474 A | 1/1991 | Bopp et al. | |
| 4,985,019 A | 1/1991 | Michelson | |
| 4,995,382 A | 2/1991 | Lang et al. | |
| 4,996,128 A | 2/1991 | Aldecoa et al. | |
| 5,010,883 A | 4/1991 | Rawlings et al. | |
| 5,018,515 A | 5/1991 | Gilman | |
| 5,025,783 A | 6/1991 | Lamb | |
| 5,028,597 A | 7/1991 | Kodama et al. | |
| 5,037,397 A | 8/1991 | Kalt et al. | |
| 5,086,170 A | 2/1992 | Luheshi et al. | |
| 5,092,323 A | 3/1992 | Riedel et al. | |
| 5,092,858 A | 3/1992 | Benson et al. | |
| 5,100,396 A | 3/1992 | Zamierowski | |
| 5,112,323 A | 5/1992 | Winkler et al. | |
| 5,134,994 A | 8/1992 | Say | |
| 5,149,331 A | 9/1992 | Ferdman et al. | |
| 5,151,314 A | 9/1992 | Brown | |
| 5,152,757 A | 10/1992 | Eriksson | |
| 5,167,613 A | 12/1992 | Karami et al. | |
| 5,176,663 A | 1/1993 | Svedman et al. | |
| 5,180,375 A | 1/1993 | Feibus | |
| 5,215,522 A | 6/1993 | Page et al. | |
| 5,232,453 A | 8/1993 | Plass et al. | |
| 5,244,457 A | 9/1993 | Karami et al. | |
| 5,246,775 A | 9/1993 | Loscuito | |
| 5,261,893 A | 11/1993 | Zamierowski | |
| 5,266,372 A | 11/1993 | Arakawa et al. | |
| 5,270,358 A | 12/1993 | Asmus | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,329 A | 8/1994 | Croquevielle | |
| 5,342,376 A | 8/1994 | Ruff | |
| 5,344,415 A | 9/1994 | DeBusk et al. | |
| 5,356,386 A | 10/1994 | Goldberg et al. | |
| 5,358,494 A | 10/1994 | Svedman | |
| 5,384,174 A | 1/1995 | Ward et al. | |
| 5,387,207 A | 2/1995 | Dyer et al. | |
| 5,419,769 A | 5/1995 | Devlin et al. | |
| 5,423,778 A | 6/1995 | Eriksson et al. | |
| 5,429,590 A | 7/1995 | Saito et al. | |
| 5,437,622 A | 8/1995 | Carion | |
| 5,437,651 A | 8/1995 | Todd et al. | |
| 5,445,604 A | 8/1995 | Lang | |
| 5,447,492 A * | 9/1995 | Cartmell ............. | A61F 13/0203 602/41 |
| 5,458,938 A | 10/1995 | Nygard et al. | |
| 5,501,212 A | 3/1996 | Psaros | |
| 5,522,808 A | 6/1996 | Skalla | |
| 5,527,293 A | 6/1996 | Zamierowski | |

(56) References Cited

U.S. PATENT DOCUMENTS

| | | |
|---|---|---|
| 5,549,584 A | 8/1996 | Gross |
| 5,549,585 A | 8/1996 | Maher et al. |
| 5,556,375 A | 9/1996 | Ewall |
| 5,585,178 A | 12/1996 | Calhoun et al. |
| 5,599,292 A | 2/1997 | Yoon |
| 5,607,388 A | 3/1997 | Ewall |
| 5,611,373 A | 3/1997 | Ashcraft |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,759,570 A | 6/1998 | Arnold |
| 5,776,119 A | 7/1998 | Bilbo et al. |
| 5,807,295 A | 9/1998 | Hutcheon et al. |
| 5,830,201 A | 11/1998 | George et al. |
| 5,878,971 A | 3/1999 | Minnema |
| 5,902,439 A | 5/1999 | Pike et al. |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,201,164 B1 | 3/2001 | Wulff et al. |
| 6,238,762 B1 | 5/2001 | Friedland et al. |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 * | 9/2003 | Dale ................ A01N 57/16 424/443 |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,197 B2 | 10/2012 | Eriksson et al. |
| 8,398,614 B2 | 3/2013 | Blott et al. |
| 8,449,509 B2 | 5/2013 | Weston |
| 8,529,532 B2 * | 9/2013 | Pinto ................ A61F 13/00029 138/30 |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,632,523 B2 | 1/2014 | Eriksson et al. |
| 8,679,081 B2 | 3/2014 | Heagle et al. |
| 8,764,732 B2 | 7/2014 | Hartwell |
| 8,834,451 B2 | 9/2014 | Blott et al. |
| 8,920,830 B2 | 12/2014 | Mathies |
| 8,926,592 B2 | 1/2015 | Blott et al. |
| 9,017,302 B2 | 4/2015 | Vitaris et al. |
| 9,192,444 B2 | 11/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,877,873 B2 | 1/2018 | Coulthard et al. |
| 9,956,120 B2 | 5/2018 | Locke |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0090496 A1 | 7/2002 | Kim et al. |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0082925 A1 | 4/2004 | Patel |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |
| 2005/0261642 A1 | 11/2005 | Weston |
| 2005/0261643 A1 | 11/2005 | Bybordi et al. |
| 2005/0277860 A1 | 12/2005 | Jensen |
| 2006/0014030 A1 | 1/2006 | Langen et al. |
| 2006/0020235 A1 | 1/2006 | Siniaguine |
| 2006/0079852 A1 | 4/2006 | Bubb et al. |

(56) References Cited

U.S. PATENT DOCUMENTS

| | | |
|---|---|---|
| 2006/0083776 A1* | 4/2006 | Bott .............. A61K 9/7084 424/445 |
| 2006/0154546 A1 | 7/2006 | Murphy et al. |
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0078366 A1 | 4/2007 | Haggstrom et al. |
| 2007/0161937 A1 | 7/2007 | Aali |
| 2007/0185426 A1 | 8/2007 | Ambrosio et al. |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2008/0009812 A1 | 1/2008 | Riesinger |
| 2008/0027366 A1 | 1/2008 | Da Silva Macedo |
| 2008/0090085 A1 | 4/2008 | Kawate et al. |
| 2008/0119802 A1 | 5/2008 | Riesinger |
| 2008/0138591 A1 | 6/2008 | Graham et al. |
| 2008/0149104 A1 | 6/2008 | Eifler |
| 2008/0173389 A1 | 7/2008 | Mehta et al. |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216168 A1 | 8/2009 | Eckstein |
| 2009/0216170 A1 | 8/2009 | Robinson et al. |
| 2009/0216204 A1 | 8/2009 | Bhavaraju et al. |
| 2009/0227969 A1 | 9/2009 | Jaeb et al. |
| 2009/0234306 A1 | 9/2009 | Vitaris |
| 2009/0234307 A1* | 9/2009 | Vitaris .............. A61M 1/0049 604/304 |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326487 A1* | 12/2009 | Vitaris .............. A61M 1/0088 604/305 |
| 2009/0326488 A1 | 12/2009 | Budig et al. |
| 2010/0028390 A1 | 2/2010 | Cleary et al. |
| 2010/0030170 A1 | 2/2010 | Keller et al. |
| 2010/0063467 A1 | 3/2010 | Addison et al. |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1 | 6/2010 | Cotton |
| 2010/0185163 A1 | 7/2010 | Heagle |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0268144 A1 | 10/2010 | Lu et al. |
| 2010/0286582 A1 | 11/2010 | Simpson et al. |
| 2010/0305490 A1 | 12/2010 | Coulthard et al. |
| 2010/0305524 A1 | 12/2010 | Vess et al. |
| 2010/0318072 A1 | 12/2010 | Johnston et al. |
| 2010/0324516 A1 | 12/2010 | Braga et al. |
| 2011/0046585 A1 | 2/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0201984 A1 | 8/2011 | Dubrow et al. |
| 2011/0224631 A1 | 9/2011 | Simmons et al. |
| 2011/0229688 A1 | 9/2011 | Cotton |
| 2011/0244010 A1 | 10/2011 | Doshi |
| 2011/0257612 A1 | 10/2011 | Locke et al. |
| 2011/0257617 A1 | 10/2011 | Franklin |
| 2011/0282309 A1 | 11/2011 | Adie et al. |
| 2012/0016322 A1 | 1/2012 | Coulthard et al. |
| 2012/0019031 A1 | 1/2012 | Bessert |
| 2012/0036733 A1 | 2/2012 | Dehn |
| 2012/0040131 A1 | 2/2012 | Speer |
| 2012/0059339 A1 | 3/2012 | Gundersen |
| 2012/0095380 A1 | 4/2012 | Gergely et al. |
| 2012/0123359 A1 | 5/2012 | Reed |
| 2012/0143157 A1 | 6/2012 | Riesinger |
| 2012/0258271 A1 | 10/2012 | Maughan |
| 2012/0310186 A1 | 12/2012 | Moghe et al. |
| 2013/0030394 A1 | 1/2013 | Locke et al. |
| 2013/0053746 A1* | 2/2013 | Roland .............. A61F 13/0289 602/44 |
| 2013/0066285 A1 | 3/2013 | Locke et al. |
| 2013/0096518 A1 | 4/2013 | Hall et al. |
| 2013/0150763 A1 | 6/2013 | Mirzaei et al. |
| 2013/0152945 A1 | 6/2013 | Locke et al. |
| 2013/0172843 A1 | 7/2013 | Kurata |
| 2013/0189339 A1 | 7/2013 | Vachon |
| 2013/0261585 A1 | 10/2013 | Lee |
| 2014/0039423 A1 | 2/2014 | Riesinger |
| 2014/0039424 A1 | 2/2014 | Locke |
| 2014/0058309 A1 | 2/2014 | Addison et al. |
| 2014/0107561 A1 | 4/2014 | Dorian et al. |
| 2014/0107562 A1 | 4/2014 | Dorian et al. |
| 2014/0141197 A1 | 5/2014 | Hill et al. |
| 2014/0155849 A1 | 6/2014 | Heaton et al. |
| 2014/0163491 A1 | 6/2014 | Schuessler et al. |
| 2014/0171851 A1 | 6/2014 | Addison |
| 2014/0178564 A1 | 6/2014 | Patel |
| 2014/0309574 A1 | 10/2014 | Cotton |
| 2014/0336557 A1 | 11/2014 | Durdag et al. |
| 2014/0350494 A1 | 11/2014 | Hartwell et al. |
| 2014/0352073 A1 | 12/2014 | Goenka |
| 2015/0030848 A1* | 1/2015 | Goubard .............. A61L 15/58 428/341 |
| 2015/0057625 A1 | 2/2015 | Coulthard |
| 2015/0080788 A1 | 3/2015 | Blott et al. |
| 2015/0080815 A1 | 3/2015 | Chakravarthy et al. |
| 2015/0119830 A1 | 4/2015 | Luckemeyer et al. |
| 2015/0119833 A1 | 4/2015 | Coulthard et al. |
| 2015/0141941 A1 | 5/2015 | Allen et al. |
| 2015/0190286 A1 | 7/2015 | Allen et al. |
| 2015/0290041 A1 | 10/2015 | Richard |
| 2016/0000610 A1 | 1/2016 | Riesinger |
| 2016/0067107 A1* | 3/2016 | Cotton .............. A61L 15/28 602/44 |
| 2016/0144084 A1 | 5/2016 | Collinson et al. |

FOREIGN PATENT DOCUMENTS

| | | |
|---|---|---|
| AU | 745271 | 4/1999 |
| AU | 755496 | 2/2002 |
| AU | 745271 B2 | 3/2002 |
| AU | 755496 B2 | 12/2002 |
| AU | 2009200608 A1 | 10/2009 |
| CA | 2005436 | 6/1990 |
| CA | 2005436 A1 | 6/1990 |
| CN | 87101823 A | 8/1988 |
| DE | 26 40 413 A1 | 3/1978 |
| DE | 43 06 478 A1 | 9/1994 |
| DE | 29 504 378 U1 | 9/1995 |
| DE | 202014100383 U1 | 2/2015 |
| EP | 097517 A1 | 1/1984 |
| EP | 0100148 A1 | 2/1984 |
| EP | 0117632 A2 | 9/1984 |
| EP | 0147119 A2 | 7/1985 |
| EP | 0161865 A2 | 11/1985 |
| EP | 0251810 A2 | 1/1988 |
| EP | 0275353 A2 | 7/1988 |
| EP | 0358302 A2 | 3/1990 |
| EP | 0538917 A1 | 4/1993 |
| EP | 0630629 A1 | 12/1994 |
| EP | 0659390 A2 | 6/1995 |
| EP | 0633758 B1 | 10/1996 |
| EP | 1002846 A1 | 5/2000 |
| EP | 1018967 A1 | 7/2000 |
| EP | 1018967 B1 | 8/2004 |
| EP | 2578193 A1 | 4/2013 |
| GB | 692578 A | 6/1953 |
| GB | 1386800 A | 3/1975 |
| GB | 2 195 255 A | 4/1988 |

(56) References Cited

FOREIGN PATENT DOCUMENTS

| | | |
|---|---|---|
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 329 127 B | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 4129536 | 4/1992 |
| JP | 2005205120 A | 8/2005 |
| JP | 2007254515 A | 10/2007 |
| JP | 2008080137 A | 4/2008 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01019306 A1 | 3/2001 |
| WO | 01/36188 A1 | 5/2001 |
| WO | 01/60296 A1 | 8/2001 |
| WO | 0168021 A1 | 9/2001 |
| WO | 0185248 | 11/2001 |
| WO | 0185248 A1 | 11/2001 |
| WO | 0190465 A2 | 11/2001 |
| WO | 01085248 A1 | 11/2001 |
| WO | 0243743 A1 | 6/2002 |
| WO | 02062403 A1 | 8/2002 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2005123170 A1 | 12/2005 |
| WO | 2007022097 A2 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008026117 A1 | 3/2008 |
| WO | 2008041926 A1 | 4/2008 |
| WO | 2008048527 A2 | 4/2008 |
| WO | 2008054312 A1 | 5/2008 |
| WO | 2008/082444 A2 | 7/2008 |
| WO | 2008100440 A1 | 8/2008 |
| WO | 2008104609 A1 | 9/2008 |
| WO | 2008/131895 A1 | 11/2008 |
| WO | 2009/002260 A1 | 12/2008 |
| WO | 2008149107 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009/124100 A1 | 10/2009 |
| WO | 2009126103 A1 | 10/2009 |
| WO | 2010016791 A1 | 2/2010 |
| WO | 2010032728 A1 | 3/2010 |
| WO | 2010/056977 A2 | 5/2010 |
| WO | 2010129299 A2 | 11/2010 |
| WO | 2011008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011130570 A1 | 10/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |
| WO | 2013090810 A1 | 6/2013 |
| WO | 2014022400 A1 | 2/2014 |
| WO | 2014039557 A1 | 3/2014 |
| WO | 2014078518 A1 | 5/2014 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |
| WO | 2017048866 A1 | 3/2017 |

OTHER PUBLICATIONS

European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion dated Jun. 1, 2011 for PCT International Application No. PCT/US2011/028344.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report dated May 22, 2014 for EP.
International Search Report and Written Opinion for PCT/US2012/069893 dated Apr. 8, 2013.
International Search Report and Written Opinion for PCT/US2013/070070 dated Jan. 29, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
Partial Internationl Search Report dated Jul. 31, 2009; PCT Internationl Application No. PCT/US2009/036222.
International Search Report and Written opinion dated Dec. 15, 2009; PCT Internation Application No. PCT/US2009/036222.
International Search Report and Written Opinion dated Feb. 24, 2010; PCT/US2009/057182.
International Search Report and Written Opinion dated Jan. 5, 2010; PCT International Application No. PCT/US2009/057130.

(56) References Cited

OTHER PUBLICATIONS

Response filed Oct. 20, 2011 for U.S. Appl. No. 12/398,904.
Interview Summary dated Oct. 27, 2011 for U.S. Appl. No. 12/398,904.
Non-Final Office Action dated Jul. 20, 2011 for U.S. Appl. No. 12/398,904.
V.A. Solovev et al., Guidelines, The Method of Treatment of Immagure External Fistulas in the Upper Gastrointestinal Tract, editor-in-chief Prov. V.I. Parahonyak (S.M. Kirov Gorky State Medican Institute, Gorky, U.S.S.R. 1987) ("Solovev Guidelines").
V.A. Kuznetsov & N.a. Bagautdinov, "Vacuum and Vacuum-Sorption Treatement of Open Septic Wounds," in All-Union Conference on Wounds and Wound Infections: Presentation Abstracts, edited by B.M. Kostyuchenok et al. (Mosco, U.S.S.R. Oct. 28-29, 1986) pp. 91-92 ("Bagautdinov II").
V.A. Solovev, Dissertation Abstract, Treatement and Prevention of Suture Failures after Gastric Resection (S.M. Kirov Gorky State Medical Institute, Gorky, U.S.S.R. 1998 ("Solovev Abstract").
NDP 1000 Negative Pressure Wound Terapy System, Kalypto Medical, pp. 1-4.
Partial International Search Report dated Jul. 31, 2009 for PCT International Application No. PCT/US2009/036217.
International Search Report and Written Opinion dated May 31, 2010 for PCT Application No. PCT/US2009/064364.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
International Search Report and Written Opinion dated Feb. 24, 2010; PCT International Application No. PCT/US2009/057182.
NPD 1000 Negative Pressure Would Therapy System, Kalypto Medical, pp. 1-4.
Partial International Search Report dated Jul. 31, 2009; PCT Internationl Application No. PCT/US2009/036222.
Non-Final Rejection for U.S. Appl. No. 12/398,904 dated Mar. 14, 2012.
International Search Report and Written Opinion for PCT/US2014/061251 dated May 8, 2015.
International Search Report and Written Opinion for PCT/IB2013/060862 dated Jun. 26, 2014.
International Search Report and Written Opinion for corresponding PCT application PCT/US2016/051768 dated Dec. 15, 2016.
International Search Report and Written Opinion for PCT/US2015/015493 dated May 4, 2015.
N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).
Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
M. Schein, R. Saadia, J.R. Jamieson, and G.A.G. Decker, "The 'Sandwich Technique' in the Management of the Open Abdomen," British Journal of Surgery 73 (1986), pp. 369-370.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
D.E. Tribble, An improved Sump Drain-Irrigation Device of Simple Construction, Archives of Surgery 105 (1972) pp. 511-513.
C.E. Tennants, "The Use of Hyperemia in the Postoperative Treatment of Lesions of the Extremities and Thorax," Journal of the American Medical Association 64 (1915), pp. 1548-1549.
International Search Report and Written Opinion for PCT/US2014/016320 dated Apr. 15, 2014.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).
European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
Office Action for related U.S. Appl. No. 13/982,650, dated Dec. 14, 2017.
Australian Office Action for related application 2013344686, dated Nov. 28, 2017.
Office Action for related U.S. Appl. No. 14/517,521, dated Dec. 12, 2017.
Office Action for related U.S. Appl. No. 14/490,898, dated Jan. 4, 2018.
International Search Report and Written Opinion for related application PCT/US2017/058209, dated Jan. 10, 2018.
Office Action for related U.S. Appl. No. 14/965,675, dated Jan. 31, 2018.
International Search Report and Written Opinion for related application PCT/US2016/047351, dated Nov. 2, 2016.
Extended European Search Report for related application 17177013.4, dated Mar. 19, 2018.
Extended European Search Report for related application 16793298.7, dated Mar. 27, 2018.
Office Action for related U.S. Appl. No. 14/965,675, dated Aug. 9, 2018.
Office Action for related U.S. Appl. No. 15/307,472, dated Oct. 18, 2018.
Office Action for related U.S. Appl. No. 14/965,675, dated Dec. 12, 2018.
Office Action for related U.S. Appl. No. 14/630,290, dated Jan. 11, 2019.
Office Action for related U.S. Appl. No. 15/265,718, dated Feb. 7, 2019.
Extended European Search Report for related application 18193559.4, dated Dec. 17, 2018.
Office Action for related U.S. Appl. No. 14/080,348, dated Apr. 12, 2019.
Japanese Notice of Rejection for related application 2016-570333, dated Feb. 26, 2019.
Office Action for related U.S. Appl. No. 15/410,991, dated May 2, 2019.
Office Action for U.S. Appl. No. 15/314,426, dated Aug. 29, 2019.
Office Action for related U.S. Appl. No. 15/600,451, dated Nov. 27, 2019.
Austrailian Office Action for related application 2018278874, dated Feb. 12, 2020.

* cited by examiner

HYBRID DRAPE HAVING A GEL-COATED PERFORATED MESH

CROSS-REFERENCE TO RELATED APPLICATIONS

This application claims priority to and the benefit of U.S. Provisional Patent Application No. 61/945,882, filed Feb. 28, 2014, entitled "HYBRID DRAPE HAVING A GEL-COATED PERFORATED MESH," to Christopher Brian Locke and Timothy Mark Robinson, which is hereby incorporated by reference.

FIELD

The present disclosure relates generally to dressings for adhering to a wound or tissue site, and more particularly, but without limitation, to a hybrid drape having a gel-coated perforated mesh.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative pressure wound therapy," "reduced-pressure therapy," "vacuum therapy," and "vacuum assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

SUMMARY

According to an illustrative, non-limiting embodiment, a dressing for treating a tissue site with negative pressure is described. The dressing may include a tissue interface configured to be positioned adjacent to the tissue site; and a sealing member configured to be positioned over the tissue interface and the tissue site to form a sealed environment. The sealing member may include a film layer, a layer of a bonding adhesive coupled to the film layer, and a mesh coupled to the layer of the bonding adhesive. The mesh may have a coating of a sealing adhesive and one or more bonding apertures.

According to another illustrative embodiment, a system for treating a tissue site with negative-pressure is described. The system may include a manifold configured to be positioned adjacent to the tissue site and a drape configured to be positioned over the tissue site and the manifold to form a sealed space. The system may also include a negative-pressure source configured to provide negative-pressure to the sealed space. The drape may include a film layer, a layer of a bonding adhesive coupled to the film layer, and a mesh coupled to the layer of the bonding adhesive. The mesh may have a coating of a sealing adhesive and one or more bonding apertures.

According to another illustrative embodiment, a method for manufacturing a drape for a negative-pressure system is described. A film layer may be provided, and a layer of a bonding adhesive may be coupled to the film layer. A mesh may be formed and coated with a sealing adhesive. One or more bonding apertures may be formed in the mesh, and the mesh may be coupled to the layer of the bonding adhesive.

Other aspects, features, and advantages of the illustrative embodiments will become apparent with reference to the drawings and detailed description that follow.

BRIEF DESCRIPTION OF THE DRAWINGS

Illustrative embodiments are described in detail below with reference to the attached drawings, which are incorporated by reference herein, and wherein.

DETAILED DESCRIPTION

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
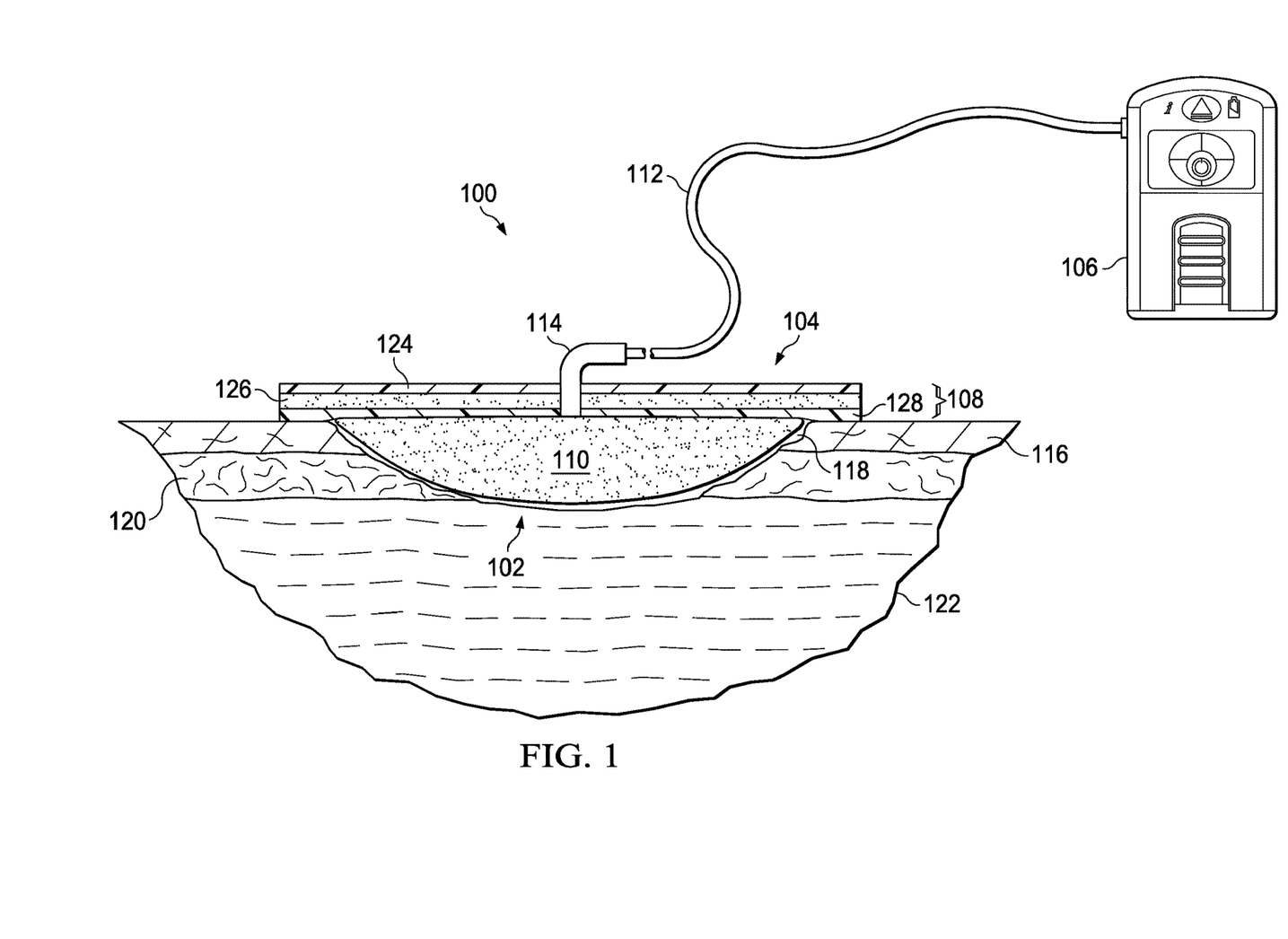
FIG. 1 is a schematic diagram of an illustrative embodiment of a system for treating a tissue site with negative pressure.

FIG. 1 is a sectional view of an example embodiment of a negative-pressure therapy system 100 illustrating details that may be associated with some embodiments for treating a tissue site 102 with negative pressure. As shown in the illustrative embodiment of FIG. 1, the negative-pressure therapy system 100 may include a dressing 104 fluidly coupled to a negative-pressure source 106. In some embodiments, the negative-pressure source 106 may be fluidly coupled to the dressing 104 by a conduit, such as a tube 112, and a connector, such as a connector 114. The dressing 104 may generally include a drape, such as a drape 108, and a tissue interface, such as a manifold 110. The drape 108 may have a film layer 124, a layer of a bonding adhesive 126, and a mesh 128. The drape 108 may be attached to an epidermis 116.

In general, components of the negative-pressure therapy system 100 may be coupled directly or indirectly to each other. For example, the negative-pressure source 106 may be directly coupled to the connector 114 and indirectly coupled to the manifold 110 through the connector 114. Components may be fluidly coupled to each other to provide a path for transferring fluids (such as, liquid, gas, or both liquid and gas) between the components.

In some embodiments, components may be fluidly coupled with a tube, such as the tube 112, for example. A "tube," as used herein, broadly refers to a tube, pipe, hose, conduit, or other structure with one or more lumina adapted to convey fluids between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, a tissue interface, such as the manifold 110, may be placed within, over, on, against, or otherwise adjacent to a tissue site. For example, the manifold 110 may be placed against the tissue site 102, and the drape 108 may be placed over the manifold 110 and sealed to tissue proximate to the tissue site 102. Tissue proximate to a tissue site is often undamaged epidermis peripheral to the tissue site. Thus, the drape 108 can provide a sealed therapeutic environment 118 proximate to the tissue site 102. The sealed therapeutic environment 118 may be substantially isolated from the external environment, and the negative-pressure source 106 can reduce the pressure in the sealed therapeutic environment 118. Negative pressure applied uniformly through a tissue interface in the sealed therapeutic environment 118 can induce macrostrain and microstrain in the tissue site 102, as well as remove exudates and other fluids from the tissue site. The removed exudates and other fluids can be collected in a container and disposed of properly.

The fluid mechanics of using a negative-pressure source to reduce pressure in another component or location, such as within a sealed therapeutic environment 118, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. This orientation is generally presumed for purposes of describing various features and components of negative-pressure therapy systems herein. Thus, in the context of negative-pressure therapy, the term "downstream" typically implies something in a fluid path relatively closer to a negative-pressure source, and conversely, the term "upstream" implies something relatively further away from a negative-pressure source. Similarly, it may be convenient to describe certain features in terms of fluid "inlet" or "outlet" in such a frame of reference. However, a fluid path may also be reversed in some applications, such as by substituting a positive-pressure source, and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desired to add or promote the growth of additional tissue. For example, negative pressure may be used in certain tissue areas to grow additional tissue that may be harvested and transplanted to another tissue location. In an illustrative embodiment, the tissue site 102 may be a wound that extends through the epidermis 116, through a dermis 120, and into subcutaneous tissue 122.

"Negative pressure" generally refers to a pressure less than a local ambient pressure, such as the ambient pressure in a local environment external to a sealed therapeutic environment 118 provided by the drape 108. In many cases, the local ambient pressure may also be the atmospheric pressure in a patient's vicinity. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 106, may be a reservoir of air at a negative pressure, or may be a manual or electrically-powered device that can reduce the pressure in a sealed volume, such as a vacuum pump, a suction pump, a wall-suction port available at many healthcare facilities, or a micro-pump, for example. A negative-pressure source may be housed within or used in conjunction with other components, such as sensors, processing units, alarm indicators, memory, databases, software, display devices, or operator interfaces that further facilitate negative-pressure therapy. While the amount and nature of negative pressure applied to a tissue site may vary according to therapeutic requirements, the pressure typically ranges between −5 millimeters of mercury (mm Hg) (−667 Pa) and −500 mm Hg (−66.7 kPa). Common therapeutic ranges are between −75 mm Hg (−9.9 kPa) and −300 mm Hg (−39.9 kPa).

A tissue interface, such as the manifold 110, can generally be adapted to contact a tissue site or other layers of a dressing. A tissue interface may be partially or fully in contact with a tissue site. If a tissue site is a wound, for example, a tissue interface may partially or completely fill the wound, or may be placed over the wound. A tissue interface may take many forms, and may be many sizes, shapes, or thicknesses depending on a variety of factors, such as the type of treatment being implemented or the nature and size of a tissue site. For example, the size and shape of a tissue interface may be adapted to the contours of deep and irregular shaped tissue sites.

In some embodiments, a tissue interface may be a manifold, such as the manifold 110. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In some embodiments, such as embodiments in which the manifold 110 may be made from a hydrophilic material, the manifold 110 may also wick fluid away from a tissue site while continuing to distribute negative pressure to the tissue site. The wicking properties of the manifold 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

A tissue interface may further promote granulation at a tissue site if pressure within the sealed therapeutic environment 118 is reduced. For example, any or all of the surfaces of the manifold 110 may have an uneven, coarse, or jagged profile that can induce microstrains and stresses at a tissue site if negative pressure is applied through the manifold 110.

In some example embodiments, a tissue interface may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface may further serve as a scaffold for new cell-growth, or a scaffold material may be used in conjunction with the tissue interface to promote cell-growth. In general, a scaffold material may be a biocompatible or biodegradable substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the drape 108 may provide a bacterial barrier and protection from physical trauma. The drape 108 may also be constructed from a material that can reduce evaporative losses and provide a fluid seal between two components or two environments, such as between a therapeutic environment and a local external environment. The drape 108 may be, for example, an elastomeric film or membrane that can provide a seal adequate to maintain a negative pressure at a tissue site for a given negative-pressure source. In some example embodiments, the drape 108 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

An attachment device may be used to attach the drape 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the drape 108 may be coated with an acrylic adhesive having a coating weight between about 25 grams per square meter (gsm) to about 65 gsm. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

A "container" broadly includes a canister, pouch, bottle, vial, or other fluid collection apparatus. A container, for example, can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy. In some embodiments, a container may be a component of a negative-pressure source, such as the negative-pressure source 106.

A "connector," such as the connector 114, may be used to fluidly couple a tube to a sealed therapeutic environment. The negative pressure developed by a negative-pressure source may be delivered through a tube to a connector. In one illustrative embodiment, a connector may be a T.R.A.C.® Pad or Sensa T.R.A.C.® Pad available from Kinetic Concepts, Inc. of San Antonio, Tex. In one exemplary embodiment, the connector 114 may allow the negative pressure generated by the negative-pressure source 106 to be delivered to the sealed therapeutic environment 118. In other exemplary embodiments, a connector may also be a tube inserted through a drape.

Negative-pressure therapy is increasingly being performed with smaller devices that use battery power rather than a connection to an electrical outlet. Use of battery power decreases the total power supply available to a device. As a result, power drains that would be considered negligible in a device powered through an electrical outlet connection may significantly reduce the performance of a battery-powered device. Power drains may be caused by low-level dressing leaks, for example, which can drain power by repeatedly triggering operation of the a negative-pressure source to maintain a therapeutic negative pressure at the tissue site. Power drains can shorten the useful life of a device by draining the device battery faster, requiring more frequent disposal of the device, recharging of the battery, or battery replacement. Leak detection techniques may help to identify some leaks that may be sealed by the user; however, low-level leaks can challenge the most sensitive leak detection systems and may often go undetected.

Low-level dressing leaks may occur between a drape and epidermis surrounding a tissue site if the drape fails to completely seal to the epidermis. Generally, a drape suitable for covering a tissue site for negative-pressure therapy may comprise a film having a thickness between about 25 microns and about 50 microns that is water-vapor permeable and formed of a polymer. The film, often formed of polyurethane, may be coated with an adhesive having a coating weight between about 25 gsm and about 65 gsm. The adhesive may often be acrylic-based and pressure sensitive. A standard acrylic adhesive may have a bond strength between about 1.8 Newton/centimeter (N/cm) and about 3.8 N/cm on stainless steel substrate at 23° C. at 50% relative humidity based on the American Society for Testing and Materials ("ASTM") standard ASTM D3330. A pressure-sensitive adhesive increases in bond strength when pressed against the surface to which the adhesive is being bonded. In some applications, a pressure-sensitive adhesive may undergo a physical change when compressed against a surface. In other applications, a pressure-sensitive adhesive may flow into crevices of a surface when compressed, increasing the bond strength without undergoing a physical change. A drape using a standard acrylic adhesive as described above is generally suitable for a dressing where a negative-pressure source powered by a continuous power supply is available to compensate for a dressing leak.

Some drapes may use a bonding adhesive instead of the standard acrylic adhesive. A bonding adhesive may be an adhesive having a bond strength that is greater than the bond strength of a standard acrylic adhesive. In some embodiments, a bonding adhesive may be a type of acrylic adhesive. A bonding adhesive may be better for sealing, but the increased bond strength may cause significantly more discomfort if the drape is removed. In addition, removing a drape having a bonding adhesive may cause significant damage to delicate or damaged skin.

A drape that has a sealing adhesive can fill gaps between the drape and the epidermis to limit leaks and can be easy to remove with low discomfort to the patient. Generally, a sealing adhesive may have a lower bond strength than a standard acrylic adhesive and a bonding adhesive. Generally, a sealing adhesive may flow into gaps and crevices more readily than a standard acrylic adhesive or a bonding adhesive. Various sealing, gap-filling adhesives, such as silicone, hydrocolloids, and hydrogels, have been used but each can have drawbacks. For example, hydrogel adhesives are usually low tack and prone to swelling, creep, and mobility when used with fluid systems. Available hydrogels and hydrocolloids may not adhere well and may move when anchored. In another example, silicone adhesives can fill gaps and seal, but are not breathable and may lose mechanical bonding strength as the silicone adhesives interact with moisture during use. To counter these problems, silicone adhesives may require additional materials to secure the silicone adhesive to a patient. For example, a low-leak drape may be formed from two adhesive layers: a thick sealing adhesive, perhaps in the shape of a gasket or ring, and a thinner bonding adhesive layer used to keep the sealing adhesive in place. Low-leak drapes constructed in this way can be more complex than a drape using a single adhesive, increasing the complexity of manipulation and operation.

A hybrid drape having a thick sealing layer that is perforated and laminated over an adhesive-coated film can overcome many of these challenges. For example, a hybrid drape may include a film layer having a bonding adhesive applied directly to the film layer, and a sealing adhesive applied directly to the bonding adhesive. The sealing adhesive can be perforated to expose the bonding adhesive. When the drape is applied to a patient, the bonding adhesive can be pushed through the perforations of the sealing adhesive to secure the sealing adhesive to the patient. This laminated configuration may provide the benefits of the sealing adhesive and the bonding adhesive over the entire drape area. For example, the laminated configuration may be conformable and of sufficient strength to ensure an initial seal, can inhibit the development of typical low-level leaks, and can mechanically affix to an epidermis without secondary processes. The laminated configuration may also minimize application care by a user and can be removable with minimal trauma to a patient.

However, construction of a laminated configuration can require additional assembly steps and can increase an amount of materials that may be needed for drape construction, which can also significantly increase costs. In addition, as two layers of adhesive are applied to the film layer, the total thickness of the drape can significantly increase, reducing breathability of the drape. Still further, as two full layers of adhesive are applied, significantly more adhesive material is needed to construct the drape.

Other hybrid drapes may register a bonding adhesive and a sealing adhesive. These hybrid drapes apply both a bonding adhesive and a sealing adhesive directly to a film layer. The bonding adhesive and the sealing adhesive may each cover different portions of a film layer to reduce the overall thickness of a hybrid drape and decrease the amount of adhesive needed to construct the hybrid drape. However, the complexity of the manufacturing process may also increase costs relative to other drapes. While using less adhesive than the laminated hybrid drapes, registered hybrid drapes may still use more adhesive in construction than standard drapes.

Some hybrid drapes may use a gel coated mesh having mesh apertures with a diameter between about 5 millimeters (mm) and about 15 mm. However, a gel-coated mesh having apertures of this size may be unable to form a seal with a tissue site. The sealing properties of the gel-coated mesh may be improved by increasing an average diameter of the fibers used to form the mesh; however, the increased diameter of the fibers may also increase a prominence of a mesh where two fibers intersect. A prominence may be a relative height of a feature compared to surrounding features. If two fibers intersect so that a first fiber overlaps a second fiber, a prominence may be a distance between a top of a first fiber and the top of the second fiber. Generally, the prominence at an intersection of two fibers may be the diameter of the largest of the two intersecting fibers. Consequently, if the diameters of the fibers are increased to increase the sealing properties of a gel-coated mesh, the raised contours associated with fiber cross-over may create leaks that are difficult to seal.

As disclosed herein, the negative-pressure therapy system 100 can overcome these challenges and others by providing a substantially flat mesh coated with a sealing adhesive. In some embodiments, for example, the drape 108 may comprise a layer of a bonding adhesive coupled to a film layer, and a mesh layer coupled to the layer of bonding adhesive. The mesh layer may be a mesh formed of small diameter fibers and can be perforated to form bonding apertures. The mesh may be coated with a sealing adhesive.

Figure 2:
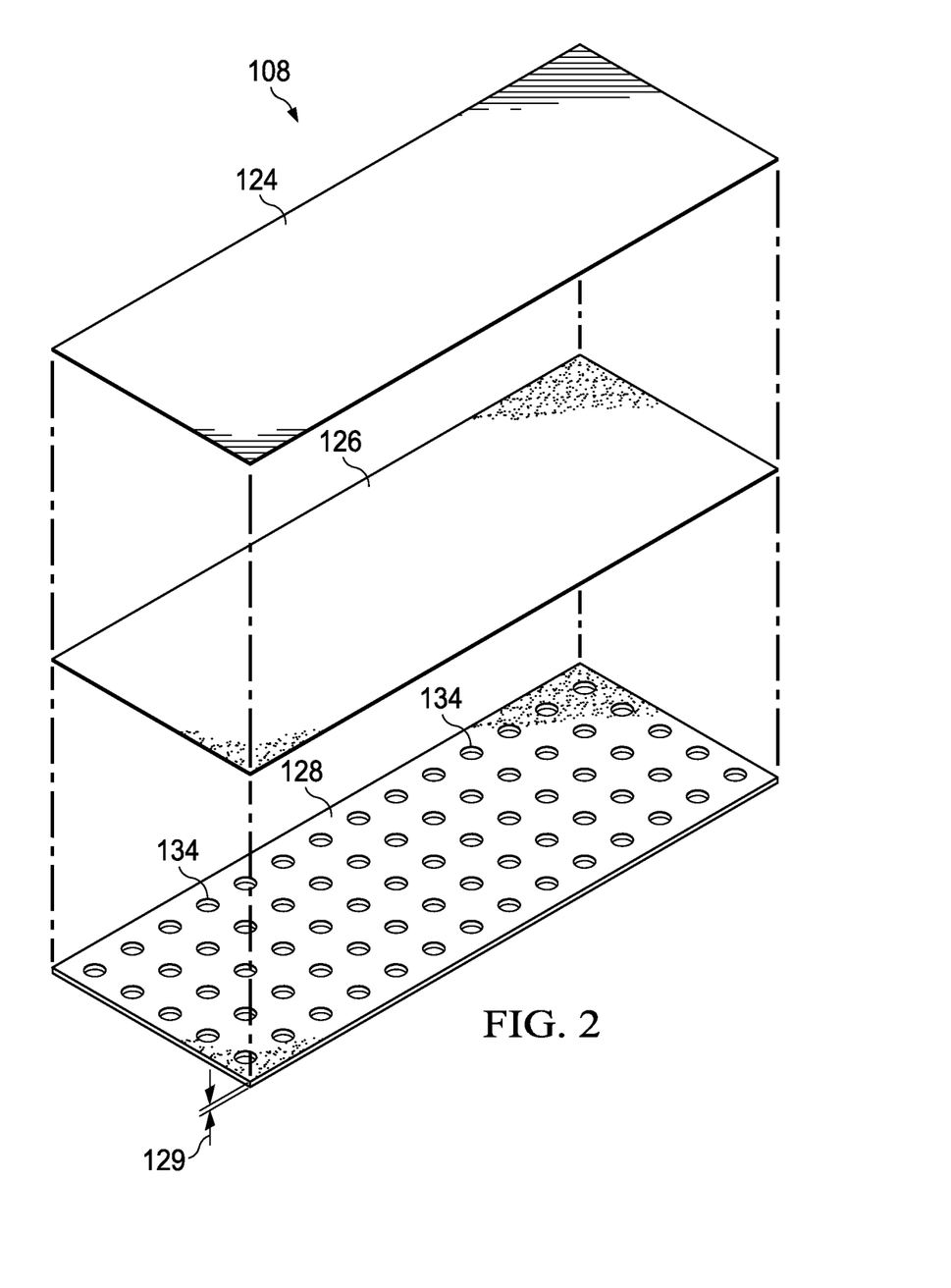
FIG. 2 is an exploded perspective view of a drape that may be used with some embodiments of the systems of FIG. 1.

FIG. 2 is an exploded perspective view, illustrating details that may be associated with some embodiments of the drape 108. The film layer 124 may be liquid-impermeable and vapor-permeable, allowing vapor to egress and inhibiting liquid from exiting. The film layer 124 may be a flexible film that is breathable and may have a high moisture-vapor transfer rate (MVTR). For example, in some embodiments, the MVTR may be greater than or equal to about 300 g/m²/24 hours. The film layer 124 may be formed from a range of medically approved films that typically range in thickness from about 15 microns (μm) to about 50 microns (μm). In other embodiments, a drape having a low MVTR or that allows no vapor transfer may be used. The film layer 124 can also function as a barrier to liquids and microorganisms.

The film layer 124 may be formed from numerous materials, such as one or more of the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. In an illustrative embodiment, the film layer 124 may be formed from a breathable cast matt polyurethane film sold by Expopack Advanced Coatings of Wrexham, United Kingdom, under the name INSPIRE 2301. The illustrative film may have an MVTR (inverted cup technique) of 14400 g/m²/24 hours and may be approximately 30 microns thick.

The bonding adhesive 126 may be coupled directly to the film layer 124. The bonding adhesive 126 may be a medically-acceptable, pressure-sensitive adhesive. For example, the bonding adhesive 126 may be formed from an acrylic adhesive, rubber adhesive, high-tack silicone adhesive, polyurethane, or other substance. In some illustrative embodiments, the bonding adhesive 126 may be formed from an acrylic adhesive with a coating weight of about 15 gsm to about 70 gsm. The bonding adhesive 126 may also be a high-bond strength acrylic adhesive, patterrubber adhesive, high-tack silicone adhesive, or polyurethane, for example. In some embodiments, the bonding adhesive 126 may have a peel adhesion or resistance to being peeled from a stainless steel material between about 6N/25 mm to about 10N/25 mm on stainless steel substrate at 23° C. at 50% relative humidity based on the ASTM D3330.

The bonding adhesive 126 may be a continuous layer of material or may be a layer with apertures (not shown). The apertures may be formed after application of the bonding adhesive 126 or may be formed by coating the bonding adhesive 126 in patterns on a carrier layer. The apertures may be sized to help control the resultant tackiness of the bonding adhesive 126. The apertures may also be sized to enhance the MVTR of the drape 108. The bonding adhesive 126 may couple the film layer 124 to the mesh 128.

In some embodiments, the mesh 128 may be a polymeric mesh, such as Mepitel® produced by Molnlycke Health Care, Adaptic® produced by Systagenix, and Noveface produced by Zodiac Aerospace Group. In some embodiments, the mesh 128 may be substantially flat. For example, the mesh 128 may have a thickness 129, and individual portions of the mesh 128 may have a minimal tolerance from the thickness 129. In some embodiments, the thickness 129 of the mesh 128 may be about 1 mm, and the tolerance of the thickness 129 may be less than about 2 mm. In another exemplary embodiment, a tolerance of the thickness 129 of the mesh 128 may be less than about 1 mm. In other embodiments, a tolerance of the thickness 129 of the mesh 128 may be less than about 0.5 mm. In some embodiments, the mesh 128 may be formed with bonding apertures 134. The bonding apertures 134 may be numerous shapes, for example, circles, squares, stars, ovals, polygons, slits, complex curves, rectilinear shapes, triangles, or other shapes.

Figure 3A:
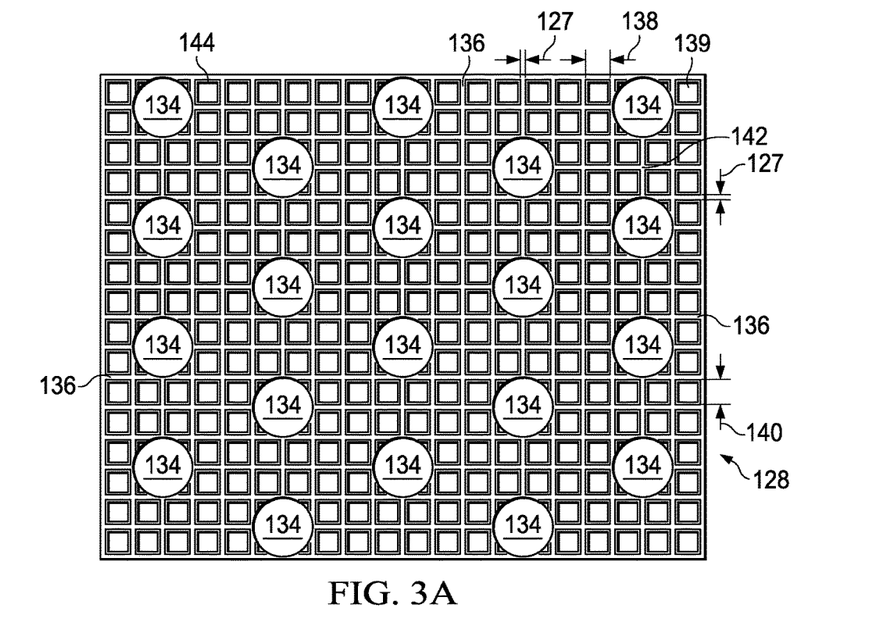
FIG. 3A is a plan view of a mesh that may be used with some embodiments of the drape of FIG. 2.

FIG. 3A is a plan view, illustrating details that may be associate with some embodiments of the mesh 128. Generally, a mesh may include a structure of connected strands of metal, fiber, or other flexible or ductile material having openings between the strands. In some embodiments, a mesh may have evenly spaced openings between adjacent strands.

In some embodiments, the mesh 128 may have a plurality of fibers 136. In some embodiments, the fibers 136 may be formed from a monofilament, a plurality of twisted monofilaments, a plurality of filaments, or a plurality of staple fibers. A filament may be a fiber that is formed in a continuous or near-continuous length. A monofilament may be a single filament. In some embodiments, a monofilament may be made from a single synthetic fiber of plastic, for example. Monofilaments may have a tensile strength related to a diameter of the monofilament and the type of material from which the monofilament is formed. A staple fiber may be a fiber of a selected standardized length, and the staple fiber may be formed of a suitable composition for used with a medical device. Each of the fibers 136 may have a diameter 127. In some embodiments, the diameter 127 may be no greater than about 1 mm. The fibers 136 may be formed from a range of materials including, but not limited to, silicone, cellulose acetate, and other similar materials.

In some embodiments, antimicrobial agents may be added to the mesh 128. In other embodiments, the fibers 136 may have antimicrobial properties. For example, in some embodiments, silver ions may be added to the fibers 136. In still other embodiments, the fibers 136 may be formed from elastomers to permit easier coverage of complex contours.

The plurality of fibers 136 may be woven, knitted, knotted, linked or otherwise connected to form a regular pattern of mesh apertures. In some embodiments, each of the plurality of fibers 136 may be separated from adjacent fibers 136 to form mesh apertures 139. In some embodiments, the fibers 136 may be separated a distance 138 from adjacent fibers, which may be between about 0.5 mm and about 4 mm. In some embodiments, each of the fibers 136 may be separated from adjacent fibers in a second direction by a distance 140. In some embodiments, the distance 140 may be between about 0.5 mm and about 4 mm. In some embodiments, the first direction of the distance 138 and the second direction of the distance 140 may be perpendicular. In some embodiments, the distance 138 and the distance 140 may be the same. In other embodiments, the first direction of the distance 138 and the second direction of the distance 140 may be other angles, and the distance 138 and the distance 140 may not be the same.

In some embodiments, the mesh apertures 139 may have an average effective diameter of about 1 mm. An effective diameter of a non-circular area may be a diameter of a circular area having the same surface area as the non-circular area. For example, the surface area of a mesh aperture 139 where the distance 138 is 0.5 mm and the distance 140 is 0.5 mm may be 0.25 mm². The diameter of a circular area having a 0.25 mm² surface area is about 0.56 mm; consequently, the effective diameter of the exemplary mesh aperture 139 is about 0.56 mm. Similarly, if the distance 138 is about 4 mm and the distance 140 is about 4 mm, the effective diameter of the mesh aperture 139 may be about 4.51 mm.

In some embodiments, the mesh 128 may include the bonding apertures 134. The bonding apertures 134 may have a uniform pattern or may be randomly distributed on the mesh 128. The bonding apertures 134 may be formed through one or more fibers 136. In some embodiments, the bonding apertures 134 may extend into the mesh apertures 139. Each bonding aperture 134 of the plurality of bonding apertures 134 may have an effective diameter. The average effective diameter of each bonding aperture 134 may be in the range of about 5 mm to about 15 mm.

In some embodiments, the mesh 128 may be coated with a gel, such as a sealing adhesive 144. In some embodiments, the sealing adhesive 144 may have a coating weight of about 100 gsm to about 500 gsm. In other embodiments, the sealing adhesive 144 may have a coating weight greater than about 200 gsm. The coating of the mesh 128 with the sealing adhesive 144 may fill in a portion of each mesh aperture 139. In some embodiments, the mesh apertures 139 may remain at least partially open after the coating of the mesh 128 with the sealing adhesive 144.

A sealing adhesive may be a soft material that provides a good seal with the tissue site 102. A sealing adhesive may be formed of a silicone gel (or soft silicone), hydrocolloid, hydrogel, polyurethane gel, polyolefin gel, hydrogenated styrenic copolymer gels, or foamed gels with compositions as listed, or soft closed cell foams (polyurethanes, polyolefins) coated with an adhesive (for example, 30 gsm-70 gsm acrylic), polyurethane, polyolefin, or hydrogenated styrenic copolymers. In some embodiments, a sealing adhesive may have a stiffness between about 5 Shore OO and about 80 Shore OO. A sealing adhesive may be hydrophobic or hydrophilic. A sealing adhesive may be an adhesive having a low to medium tackiness, for example, a silicone polymer, polyurethane, or an additional acrylic adhesive. In some embodiments, a sealing adhesive may a bond strength between about 0.5N/25 mm and about 1.5N/25 mm on a stainless steel substrate at 23° C. at 50% relative humidity based on ASTM D3330. A sealing adhesive may have a tackiness such that the sealing adhesive may achieve the bond strength above after a contact time of less than 60 seconds. Tackiness may be considered a bond strength of an adhesive after a very low contact time between the adhesive and a substrate. In an illustrative embodiment, a sealing adhesive may have a tackiness that may be about 30% to about 50% of the tackiness of a bonding adhesive.

In some embodiments, the bonding apertures 134 may be formed prior to coating of the mesh 128 with the sealing adhesive 144. In other embodiments, the bonding apertures 134 may be formed in the mesh 128 following coating of the mesh 128 with the sealing adhesive 144.

In some embodiments, the fibers 136 of the mesh 128 may form a plurality of intersections 142. In some embodiments, an intersection 142 may be a location of the mesh 128 where at least two fibers 136 overlap, cross-over, or meet, for example.

Figure 3B:
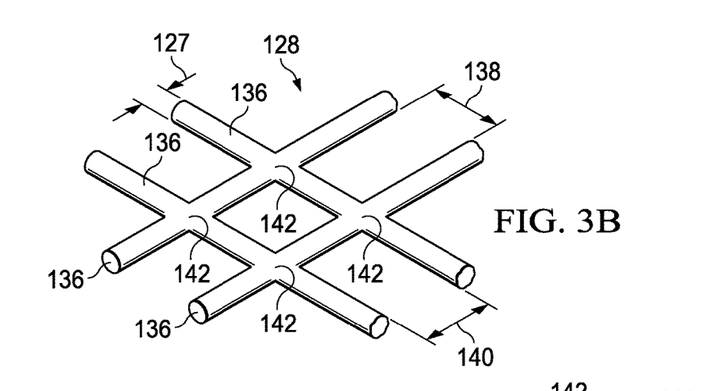
FIG. 3B is a perspective view of a portion of the mesh of FIG. 3A.

FIG. 3B is a perspective view, illustrating additional details that may be associated with some embodiments of the mesh 128 of FIG. 3A. In some embodiments, the mesh 128 may be formed so that at each intersection 142, the intersecting fibers 136 may be fused so that the intersection 142 is planar. In some embodiments, the mesh 128 may be molded, extruded, or expanded to form the mesh 128. In embodiments where the mesh 128 is molded, extruded, or expanded, the fibers 136 at an intersection 142 may be fused or joined so that a prominence at the intersection 142 is less than about 1 mm. In some embodiments, the prominence at an intersection 142 may be about 0 mm. In some embodiments, a substantially flat mesh may have a thickness at the intersections 142 that may be substantially the same as a thickness of the mesh 128 surrounding the intersections 142.

Figure 3C:
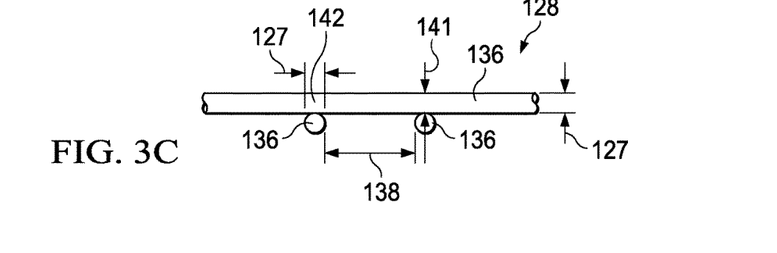
FIG. 3C is a side elevation view of a portion of the mesh of FIG. 3A.

FIG. 3C is a side elevation view, illustrating additional details that may be associated with some embodiments of the mesh 128. In some embodiments, the mesh 128 may be formed by weaving or knitting the fibers 136. If the fibers 136 are woven or knitted, the intersections 142 may have a prominence 141. In some embodiments, the prominence 141 of the fibers 136 at the intersections 142 may be equal to the diameter 127 of the fibers 136. In some embodiments, the prominence 141 may be reduced by compressing the mesh 128 following weaving or knitting the fibers 136. The prominences 141 of the fibers 136 may also be reduced by passing the mesh 128 through a calender, which may apply pressure to the mesh 128 to smooth out the mesh 128. In some embodiments, the prominence 141 may be less than about 1 mm.

Figure 4:
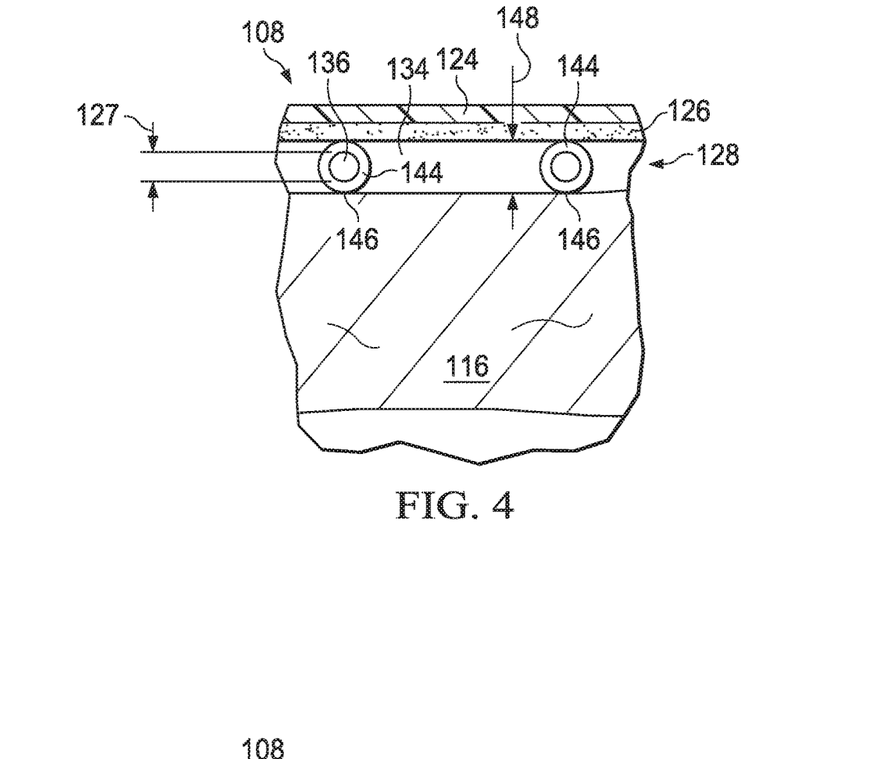
FIG. 4 is a sectional view illustrating additional details that may be associated with some embodiments of the drape of FIG. 2 in a first state.

FIG. 4 is a sectional view, illustrating additional details that may be associated with some embodiments of the drape 108. In the assembled state, the bonding adhesive 126 may be coupled to the film layer 124, and the mesh 128 may be coupled to the bonding adhesive 126. If the mesh 128 is placed proximate to or in contact with the epidermis 116, the sealing adhesive 144 coating the mesh 128 may form sealing couplings 146 with the epidermis 116. In some embodiments, the diameter 127 of the fibers 136, the thickness of the sealing adhesive 144, and the bonding apertures 134 may create a gap 148 between the bonding adhesive 126 and the epidermis 116.

Figure 5:
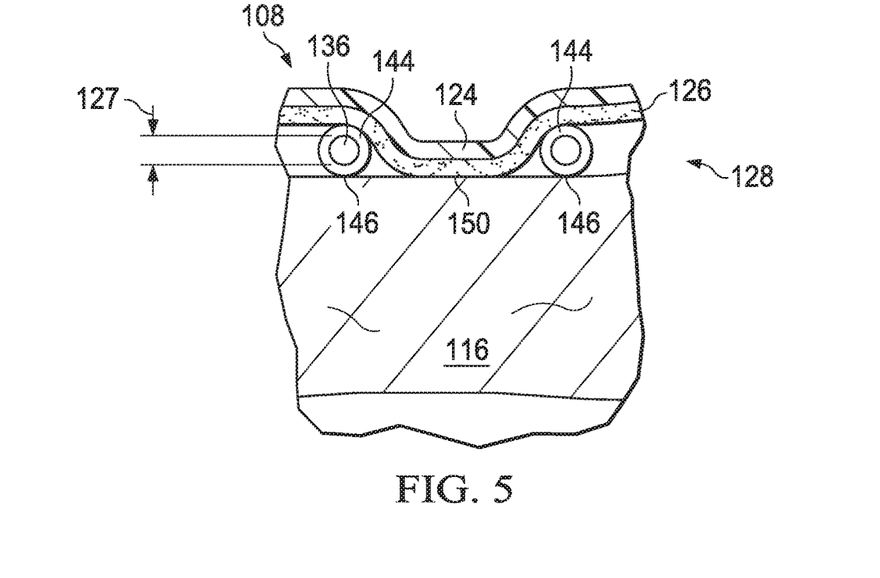
FIG. 5 is a sectional view of the portion of the drape of FIG. 4 in a second state.

FIG. 5 is a sectional view, illustrating additional details that may be associated with some embodiments of the drape 108 of FIG. 4 in a second position. If the drape 108 is in a desired location, pressure may be applied to the film layer 124. The pressure may cause the bonding adhesive 126 to be pressed at least partially into contact with the epidermis 116 to form bonding couplings 150. The bonding couplings 150 may provide secure, releasable mechanical fixation to the epidermis 116. The sealing couplings 146 between the sealing adhesive 144 and the epidermis 116 may be sufficient to seal the film layer 124 to the epidermis 116. The sealing couplings 146 may not be as mechanically strong as the bonding couplings 150 between the bonding adhesive 126 and the epidermis 116. The bonding couplings 150 may also anchor the drape 108 to the epidermis 116, inhibiting migration of the drape 108 and the sealing adhesive 144.

The average effective diameter of the bonding apertures 134 of the sealing adhesive 144 may be varied as one control of the tackiness or adhesion strength of the drape 108. In this regard, there may be an interplay between three main variables for each embodiment: the diameter 127 of the fibers 136, the average effective diameter of the plurality of bonding apertures 134, and the tackiness of the bonding adhesive 126. The more bonding adhesive 126 that extends through the bonding apertures 134, the stronger the bonding coupling 150. The smaller the diameter 127 of the fibers 136, the more the bonding adhesive 126 generally extends through the bonding apertures 134 and the greater the bonding coupling 150. As an example of the interplay, if a very tacky bonding adhesive 126 is used and the diameter 127 of the fibers 136 of the mesh 128 is small, the average effective diameter of the plurality of bonding apertures 134 may be relatively smaller to maintain a same adhesion strength of the drape 108.

In other embodiments, the mesh 128 may be formed from a perforated film which is then coated with the sealing adhesive 144 and laminated to the film layer 124 or the bonding adhesive 126. In other embodiments, the mesh 128 may be coated with the bonding adhesive 126 and then pattern-coated with the sealing adhesive 144. The mesh 128 may then be laminated directly to the film layer 124. The bonding adhesive 126 may be exposed through the areas of the mesh 128 that were not pattern-coated with the sealing adhesive 144.

In some embodiments, the adhesives may be mixed with blowing or expanding agents, for example organic and inorganic low temperature boiling point liquids. The blowing or expanding agents allow for the adhesives to expand under the application of heat or light to increase the thickness of the adhesive following deposition by one of the above described processes. The blowing or expanding agents may reduce the amount of adhesive needed and decrease the cost of production. In some embodiments, the application of heat or light may be delayed until application of the drape 108 to the epidermis 116 so that the contact area with the epidermis 116 may increase as the bonding adhesive 126 and the sealing adhesive 144 warm by contact with the epidermis 116. The application of light or heat following application of the drape 108 to the epidermis 116 can provide a better seal for some embodiments of the drape 108 to the epidermis 116.

A drape having a coated mesh may provide a lower cost solution that makes more efficient use of a sealing adhesive. The increase in efficiency of the use of a sealing adhesive may be accomplished without the complication of adding extruders and pattern coaters that may be required for pattern printing of adhesives. A drape having a coated mesh may have a higher MVTR than other drapes as the inclusion of mesh apertures can permit greater passage of moisture without interfering with sealing.

Although certain features and their advantages have been disclosed in the context of certain illustrative, non-limiting embodiments, it should be understood that various changes, substitutions, permutations, and alterations can be made without departing from the scope of the appended claims. It will be appreciated that features that may be described in connection to one embodiment may also be applicable to other embodiments. It will also be understood that the benefits and advantages described above may relate to one embodiment or may relate to several embodiments. It will further be understood that reference to "an" item refers to one or more of those items.

The steps of the methods described herein may be carried out in a suitable order, or simultaneously where appropriate.

Where appropriate, aspects of the embodiments described above may be combined with aspects of the other embodiments described to form further examples having comparable or different properties and addressing the same or different problems.

It will be understood that the embodiments described herein are given by way of example only and that various modifications may be made by those skilled in the art. The above specification, examples and data provide a complete description of the structure and use of exemplary embodiments. Although various embodiments have been described above with a certain degree of particularity, or with reference to one or more individual illustrations, those skilled in the art could make numerous alterations to the example embodiments without departing from the scope of the claims.

We claim:

1. A dressing for treating a tissue site with negative pressure, the dressing comprising:
a manifold configured to be positioned adjacent to the tissue site, the manifold having a plurality of pathways configured to distribute negative pressure across the tissue site; and
a sealing member configured to be positioned over the tissue interface and the tissue site to form a sealed environment, the sealing member comprising:
a film layer having a first side and a second side,
a layer of a bonding adhesive having a first side coupled to the second side of the film layer and a second side, and
a mesh coupled to the second side of the layer of the bonding adhesive, the mesh having a coating of a sealing adhesive and one or more bonding apertures, wherein the film layer, the layer of the bonding adhesive, and the mesh are congruent layers and the layer of the bonding adhesive separates the film layer from the mesh.

2. The dressing of claim 1, wherein the mesh comprises a plurality of fibers connected to form intersections.

3. The dressing of claim 2, wherein each intersection of the fibers is substantially flat.

4. The dressing of claim 2, wherein a prominence of the fibers at each intersection is less than about 1 millimeter.

5. The dressing of claim 2, wherein the fibers are woven.

6. The dressing of claim 2, wherein the fibers are knitted.

7. The dressing of claim 2, wherein the fibers are extruded and are substantially planar at each intersection.

8. The dressing of claim 2, wherein a diameter of each fiber of the plurality of fibers is less than about 1 millimeter.

9. The dressing of claim 2, wherein each fiber of the plurality of fibers is a monofilament.

10. The dressing of claim 2, wherein each fiber of the plurality of fibers is a plurality of twisted monofilaments.

11. The dressing of claim 2, wherein each fiber of the plurality of fibers is a plurality of staple fibers.

12. The dressing of claim 1, wherein the mesh has a plurality of mesh apertures.

13. The dressing of claim 12, wherein an effective diameter of each mesh aperture is between about 0.5 millimeters and about 4 millimeter.

14. The dressing of claim 1, wherein a coating weight of the coating of the sealing adhesive is between about 100 grams per square meter and about 500 grams per square meter.

15. The dressing of claim 1, wherein an effective diameter of each bonding aperture is between about 5 millimeter and about 15 millimeter.

16. The dressing of claim 1, wherein the mesh comprises a polymeric mesh.

17. The dressing of claim 1, wherein:
the film layer comprises a polyurethane film having a thickness between about 15 microns and about 50 microns;
the bonding adhesive comprises an acrylic adhesive having a coating weight between about 15 grams per square meter and about 70 grams per square meter;
the mesh comprises a silicone mesh having mesh apertures with an effective diameter between about 0.5 millimeters and about 4.5 millimeters; and
the sealing adhesive comprises a silicone gel adhesive having a coating weight between about 100 grams per square meter and about 500 grams per square meter.

18. A system for treating a tissue site with negative-pressure, the system comprising:
a manifold configured to be positioned adjacent to the tissue site, the manifold having a plurality of pathways configured to distribute negative pressure across the tissue site;
a drape configured to be positioned over the tissue site and the manifold to form a sealed space; and
a negative-pressure source configured to provide negative-pressure to the sealed space;
wherein the drape comprises:
a film layer having a first side and a second side,
a layer of a bonding adhesive having a first side coupled to the film layer and a second side,
a mesh coupled to the second side of the layer of the bonding adhesive, the mesh having a coating of a sealing adhesive and one or more bonding apertures, wherein the film layer, the layer of the bonding adhesive, and the mesh are congruent layers and the layer of the bonding adhesive separates the film layer from the mesh.

19. The system of claim 18, wherein the mesh comprises a plurality of fibers connected to form intersections.

20. The system of claim 19, wherein each intersection of the fibers is substantially flat.

21. The system of claim 19, wherein a prominence of the fibers at each intersection is less than about 1 millimeter.

22. The system of claim 19, wherein the fibers are woven.

23. The system of claim 19, wherein the fibers are knitted.

24. The system of claim 19, wherein the fibers are extruded and are substantially planar at each intersection.

25. The system of claim 19, wherein a diameter of each fiber of the plurality of fibers is less than about 1 millimeter.

26. The system of claim 19, wherein each fiber of the plurality of fibers is a monofilament.

27. The system of claim 19, wherein each fiber of the plurality of fibers is a plurality of twisted monofilaments.

28. The system of claim 19, wherein each fiber of the plurality of fibers is a plurality of staple fibers.

29. The system of claim 18, wherein the mesh has a plurality of mesh apertures.

30. The system of claim 29, wherein an effective diameter of each mesh aperture is between about 0.5 millimeter and about 4 millimeter.

31. The system of claim 18, wherein a coating weight of the coating of the sealing adhesive is between about 100 grams per square meter and about 500 grams per square meter.

32. The system of claim 18, wherein an effective diameter of each bonding aperture is between about 5 millimeter and about 15 millimeter.

33. The system of claim 18, wherein the mesh comprises a polymeric mesh.

34. The system of claim 18, wherein:
the film layer comprises a polyurethane film having a thickness between about 15 microns and about 50 microns;
the bonding adhesive comprises an acrylic adhesive having a coating weight between about 15 grams per square meter and about 70 grams per square meter;
the mesh comprises a silicone mesh having mesh apertures with an effective diameter between about 0.5 millimeters and about 4.5 millimeters; and
the sealing adhesive comprises a silicone gel adhesive having a coating weight between about 100 grams per square meter and about 500 grams per square meter.

\* \* \* \* \*